US008206686B2

(12) United States Patent
Rau

(10) Patent No.: US 8,206,686 B2
(45) Date of Patent: Jun. 26, 2012

(54) ORGANIC ACID FREE EFFERVESCENT FORMULATION

(75) Inventor: Allen H. Rau, Cincinnati, OH (US)

(73) Assignee: Tower Laboratories, Ltd., Centerfrook, CT (US)

( * ) Notice: Subject to any disclaimer, the term of this patent is extended or adjusted under 35 U.S.C. 154(b) by 259 days.

(21) Appl. No.: 12/425,458

(22) Filed: Apr. 17, 2009

(65) Prior Publication Data

US 2010/0074849 A1 Mar. 25, 2010

Related U.S. Application Data

(60) Provisional application No. 61/099,221, filed on Sep. 23, 2008.

(51) Int. Cl.

| | |
|---|---|
| ***A61K 9/12*** | (2006.01) |
| ***A61K 8/00*** | (2006.01) |
| ***C09K 3/00*** | (2006.01) |
| ***C11D 3/02*** | (2006.01) |

(52) U.S. Cl. ................ 424/44; 252/182.11; 252/182.35; 510/108; 510/507; 510/509; 512/1

(58) Field of Classification Search ........................ None
See application file for complete search history.

(56) References Cited

U.S. PATENT DOCUMENTS 4,409,118 A * 10/1983 Eoga ............................ 510/117
5,993,854 A * 11/1999 Needleman et al. .......... 424/466

* cited by examiner

*Primary Examiner* — Fereydoun G Sajjadi
*Assistant Examiner* — David Browe
(74) *Attorney, Agent, or Firm* — Steven B. Kelber; Berenato & White, LLC

(57) ABSTRACT

This invention provides a tablet that effervesces and significantly warms the water that it is dissolved in. The effervescence acts to break up the tablet allowing an exothermic material to rapidly dissolve releasing its heat of solution. The invention is unique in that no organic acid is required to form a conventional effervescent couple.

11 Claims, No Drawings

ORGANIC ACID FREE EFFERVESCENT FORMULATION

PRIORITY DATA AND INCORPORATION BY REFERENCE

This application claims benefit of priority to U.S. Provisional Patent Application No. 61/099,221 filed Sep. 23, 2008, which is incorporated by reference in its entirety.

BACKGROUND OF THE INVENTION

Field of the Invention

The intent of the present invention is to create a composition that, while effervescing, will increase the temperature of the water that it is in by about 20° C. for 200 grams of water. The composition is preferably n the form of a tablet, but might conveniently be presented as a water soluble capsule, granule, or dense flowing powder, using established technology. The inventive composition is particularly characterized in that it is free of organic acid effervescing components.

U.S. Pat. No. 5,993,854 describes an exothermic effervescent tablet that is designed to improve the dispersion of volatile materials. The invention described in that patent uses the combination of an exothermic material (a material that has positive heat of solution when placed in water) and a conventional effervescent couple. A conventional effervescent couple is defined as the combination of a carbonate salt and an organic acid. Typical carbonate salts are bicarbonates or carbonates. The sodium, potassium, magnesium and calcium forms are most common. Organic acids such as citric acid, fumaric acid, tartaric acid, adipic acid, succinic acid and malic acid are frequently used as the organic acid component.

While certain compositions within the technology of the '854 patent may be able to be used to achieve the invention's goal of warming water while effervescing, they are not optimal solutions for the purpose of specifically warming the water or liquid. This is because the effervescent reaction is endothermic (as shown by data in that patent) and thus a significant fraction of the heat generated by the exothermic material goes to warming the water or liquid cooled by the endothermic effervescent reaction.

It would be desirable to provide a simple composition that can provide a rapid and significant heat increase to water or a water-based liquid in which it is dissolved. In general, a target heat elevation of 20° C. in five minutes is the goal of this invention. While various commercial and non-commercial applications will call for various heating regimens, a heat increase of from room temperature 30 or 35° C. within 5 minutes for 150 or 200 ml of water is achievable using the same formulations. This invention overcomes the drawback of using and endothermic effervescence reaction, and achieves the targets for this application, by using exothermic materials which are capable of initiating the effervescent reaction with a carbonate salt in the absence of the organic acid which is typically used for that purpose.

DETAILED DESCRIPTION

By definition, 1 calorie is the amount of heat needed to raise 1 gram of water 1° C. Therefore 6000 calories (6 kcal) are needed to heat 200 grams of water by 30° C. Obviously, all things being equal, a lesser amount is required to elevate the temperature of the same water by at least 20° C., which is the general target of the invention. More broadly, the invention addresses compositions, preferably tablets, which cause water of aqueous liquids in which they are placed to warm and effervesce, without the aid or presence of an organic acid.

The amount of a given exothermic material needed to generate 6 kcal is easily calculated from the heat of solution data found in Lange's Handbook of Chemistry, 11$^{th}$ edition, Table 9-6:

$$\text{Amount needed}=6\ \text{kcal}/(\text{kcal/gm-mole liberated})\times\text{molecular weight}$$

This amount was calculated for several commercially important materials:

| Material | kcal/gm-mole liberated | MW | Required amount (g) |
|---|---|---|---|
| $MgCl_2$ | 35.9 | 95.2 | 15.9 |
| $MgSO_4$ | 20.3 | 120.4 | 35.6 |
| $CaCl_2$ | 17.4 | 111.0 | 38.3 |

Each of these materials was combined individually with various carbonate salts. Tablets were formed by compressing the binary mixtures using a hand operated hydraulic (Carver) press at approximately 3000 psi. Density is not a critical aspect of the invention, low density tablets of at least 1.0 g/cc and above will be suitable. The resulting tablets were placed in approximately 200 g of water. The temperature change and effervescent properties were noted. Note: in some cases the size of the tablet and amount of water used was scaled up or down in appropriate ratio in order to accommodate the availability of materials and/or to physically be able to press a tablet. Data are:

| Exothermic Material | grams Exothermic Material | Carbonate Salt | grams Carbonate Salt | Effervescence | Temperature Rise (° C.) | Comments |
|---|---|---|---|---|---|---|
| $MgCl_2$ | 16 | $NaHCO_3$ | 10 | Yes | 25 | |
| $MgCl_2$ | 16 | $NaHCO_3$ | 5 | Yes | 25 | |
| $MgCl_2$ | 21 | $NaHCO_3$ | 5 | Yes | 32 | |
| $MgCl_2$ | 16 | $Na_2CO_3$ | 10 | V. Slight | 15 | Incomplete dissolution |
| $MgCl_2$ | 16 | $KHCO_3$ | 10 | Yes | 22 | |
| $MgCl_2$ | 16 | $K_2CO_3$ | 10 | V. Slight | 16 | Incomplete dissolution |
| $MgSO_4$ | 3.6 | $NaHCO_3$ | 1 | Slight | 9 | 20 ml $H_20$, Incomplete dissolution |
| $CaCl_2$ | 19.5 | $NaHCO_3$ | 5 | Yes | 6 | 100 ml $H_20$, Incomplete dissolution |

-continued

| Exothermic Material | grams Exothermic Material | Carbonate Salt | grams Carbonate Salt | Effervescence | Temperature Rise (° C.) | Comments |
|---|---|---|---|---|---|---|
| $MgCl_2$ | 16 | $NaHCO_3$ | 20 | None | 16 | Incomplete dissolution |

The finding that effervescence could be generated without the use of an organic acid was very surprising, and contrary to a vast amount of literature which assumes that effervescence is produced by combining a carbonate salt with an acid, particularly an organic acid. The effervescence is clearly important as it helps the tablet dissolve. In experiments where the effervescence was minimal or non-existent, the temperature rise is much lower than where the tablet is broken up by carbon dioxide gas generation. Viewed at from the point of view of the exothermic release—it is clear that the heat provided drives the effervescence to at least some degree. Thus, full effervescence can be observed in the absence of an organic acid component. In turn, the generated effervescence drives an improved heat release, or exothermic release. Without wishing to be bound by this explanation, it is theorized that the effervescence aids in breaking up the exothermic component in the tablet, exposing more surface area and improving/accelerating its dissolution. The two components of this composition synergistically improve performance. Clearly, the performance of the tablet or composition of the invention, and its use as a composition to elevate the temperature of liquid with effervescence, balances the properties and characteristics of the exothermic agent and the carbonate/bicarbonate salt.

These appearance of effervescence is especially surprising given that the pH of each of the tested exothermic materials is at most very weakly acidic (one familiar with the art and technology of effervescence would not expect carbonate salts to react with alkaline or very weakly acid materials to liberate carbon dioxide):

| Material | pH at 5% w/w |
|---|---|
| $MgCl_2$ | 8.7 |
| $MgSO_4$ | 8.8 |
| $CaCl_2$ | 6.4 |

Although these examples are aimed at generating temperature rises of about 20-30° C. in 200 grams of water, it is clear that the amounts and ratios of the exothermic material and carbonate salt can be adjusted and balanced to give just about any temperature increase in just about any amount of water. The inventive composition may be in the form of a tablet, granule or powder. The tablet forming process starts with powders, and both MgCl and e.g., sodium bicarbonate, are available as free flowing powders. Combined as powders and dissolved together, they will raise the temperature of water they are dissolved in. Similarly, since tableting is a step typically performed by compressing granules, the composition of the invention may preferably be used in the form of granules. Granules are prepared from thoroughly mixed appropriate weight amounts of the various powdered starting materials (e.g., magnesium chloride and sodium bicarbonate). Methods of preparing granules are known to those of skill in the art, and are generally categorized into dry granulation (typically applied to free flowing powders), wet granulation (where typically the lubricant, glidant, possibly an antiadherent and binder are added in the granulation process, which may include a binder) and fluidized bed granulation, which may offer more control. Granules also come in a large range of densities. For the purposes of this invention, densities in excess of 1.0 g/cc, and specifically of about 1.2 g/cc or greater, are preferable. For a comparison of granulation technologies, the granules produced and resulting tablets, see Kristensen et al, *AAPS PharmSciTech* 2006:7(1)pp. E1-E10 (2006) incorporated herein by reference.

It must be noted that the binary compositions shown above are not intended to be used as consumer products "as is". Additional materials will need to be added to allow commercial production, deliver functional benefits, and to have acceptable aesthetics for their intended use.

Some examples of materials of materials that may be combined with exothermic/effervescent mixture are: binders, lubricants, flow aides, surfactants, bleaches, enzymes, fragrances and colorants.

Some common binders include, but are not limited to: sorbitol, mannitol, dextrose, sucrose, maltodextrin, corn syrup solids, dicalcium phosphate, and microcrystalline cellulose.

Potential lubricants include, but are not limited to: polyethylene glycol, magnesium stearate, sodium benzoate, leucine, talc, fumaric acid, and corn starch.

Typical flow aides include, but are not limited to, fumed silica and calcium silicate.

Surfactants may include, but are not limited to: sodium lauryl sulfate, sodium lauryl ethoxy sulfates, sodium lauryl sulfoacetate, sodium dodecyl benzene sulfonate, alpha olefin sulfonate, sodium lauryl sulfosuccinate, various fatty alcohols and fatty alcohol ethoxylates, and nonylphenol ethoxylates.

Bleaches that may be used include, but are not limited to: sodium perborate, potassium caroate (Oxone™), sodium percarbonate, urea peroxide and calcium peroxide.

Enzymes may include, but are not limited to: protease, amylase, lipase, and cellulase.

Given the above possibilities, it is clear that the invention may be used in place of existing technologies wherever effervescence is an important or essential aspect of the composition, either functionally or aesthetically, and the resulting liquid is suitably warmed for use. Examples include the following formulations:

EXAMPLE 1

Water Heating Tablet (Could be Used to Warm Food Contained in a Pouch)

| Material | grams | % w/w |
|---|---|---|
| Magnesium Chloride | 20.00 | 78.44 |
| Sodium Bicarbonate | 5.00 | 19.60 |

-continued

| Material | grams | % w/w |
|---|---|---|
| Polyethylene Glycol 8000 | 0.25 | 0.98 |
| Sodium Benzoate | 0.25 | 0.98 |
| Total | 25.50 | 100.00 |

Evaluation: When dissolved in 200 ml water temperature rise was 29° C.

EXAMPLE 2

Aroma Diffusing Tablet

| Material | grams | % w/w |
|---|---|---|
| Magnesium Chloride | 10.00 | 57.13 |
| Sodium Bicarbonate | 2.50 | 14.30 |
| Polyethylene Glycol 8000 | 0.12 | 0.71 |
| Sodium Benzoate | 0.13 | 0.71 |
| Fragrance | 0.75 | 4.29 |
| Maltodextrin | 4.00 | 22.86 |
| Color | As desired | As desired |
| Total | 17.50 | 100.00 |

Evaluation: When dissolved in 100 ml water temperature rise was 25° C.

EXAMPLE 3

Jewelry Cleaning Tablet

| Material | grams | % w/w |
|---|---|---|
| Magnesium Chloride | 6.00 | 60.00 |
| Sodium Bicarbonate | 2.00 | 20.00 |
| Polyethylene Glycol 8000 | 0.10 | 1.00 |
| Sodium Benzoate | 0.10 | 1.00 |
| Sodium Lauryl Sulfate | 0.10 | 1.00 |
| Tetrasodium EDTA | 0.50 | 5.00 |
| Fragrance | 0.20 | 2.00 |
| Maltodextrin | 1.00 | 10.00 |
| Color | As desired | As desired |
| Total | 10.00 | 100.00 |

Evaluation: When dissolved in 50 ml water temperature rise was 23° C.

EXAMPLE 4

Cleaning Tablet with Oxygen Bleach

| Material | Grams | % w/w |
|---|---|---|
| Magnesium Chloride | 20.00 | 66.67 |
| Sodium Bicarbonate | 5.00 | 16.67 |
| Polyethylene Glycol 8000 | 0.25 | 0.83 |
| Sodium Benzoate | 0.25 | 0.83 |
| Sodium Lauryl Sulfate | 0.01 | 0.03 |
| Potassium Caroate (Oxone ®) | 0.60 | 2.00 |

-continued

| Material | Grams | % w/w |
|---|---|---|
| Sodium Perborate | 0.60 | 2.00 |
| Fragrance | 0.20 | 0.67 |
| Maltodextrin | 3.09 | 10.30 |
| Color | As desired | As desired |
| Total | 30.00 | 100.00 |

Evaluation: When dissolved in 200 ml water temperature rise was 26° C.

EXAMPLE 5

Enzymatic Cleaning Tablet

| Material | grams | % w/w |
|---|---|---|
| Magnesium Chloride | 10.00 | 66.66 |
| Sodium Bicarbonate | 2.50 | 16.67 |
| Polyethylene Glycol 8000 | 0.15 | 1.00 |
| Sodium Benzoate | 0.14 | 0.93 |
| Sodium Lauryl Sulfoacetate | 0.01 | 0.07 |
| Potassium Caroate (Oxone ®) | 0.60 | 4.00 |
| Sodium Perborate | 0.60 | 4.00 |
| Protease Enzyme | 0.04 | 0.27 |
| Fragrance | 0.10 | 0.67 |
| Sorbitol | 0.86 | 5.73 |
| Color | As desired | As desired |
| Total | 15.00 | 100.00 |

Evaluation: When dissolved in 100 ml water temperature rise was 21° C.

Clearly, those of ordinary skill in the art will recognize that there are combinations of carbonate salt and exothermic material that will achieve the desired goal, in addition to the formulations advanced. As one example, reference may be had to the use of zeolites. These sodium alumino silicates generate a large degree of heat when contacted with water. They are also capable of storing large amounts of water, so that compositions prepared from zeolite-based exothermic reactants should not be as liquid sensitive as others. Zeolites, particularly Class 3 and 4, but 5 and X as well, are put to a vast range of commercial uses.

By the same token, the choice of an appropriate carbonate for the generation of $CO_2$ is not particularly limited. As noted above, the $CO_2$ release is tied to the ability to rapidly raise the temperature of the liquid in which the composition is immersed. To this end bicarbonates are more effective, weight for weight, than carbonates. The sodium, potassium, magnesium and calcium bicarbonates are preferable for the applications envisioned. Given adequate exothermic content (generally, the amount of MgCl or zeolite included) the amount of bicarbonate called for can be calculated.

A variety of applications are described above. The tablet may be used in large scale commercial operations—everything from jewelry cleaning to cleaning the interior of boilers and other surfaces where scaling may occur, notably constricted passageways and similar applications. Aroma therapy, particularly the use of aromas to fill a constrained space, such as a room in a dwelling, is supported by the disclosed invention. The tablet is far more portable than a variety of heating alternatives, and can, for example, be used to raise the temperature of water when camping or otherwise cut off from sources of electricity. This may be convenient for, e.g., hand washing or skin cleansing. These are conventional applications. The heart of the invention resides in a composition, preferably a tablet, which comprises an exothermic component, preferably MgCl or a zeolite, and a bicarbonate salt, but is free of an organic acid component yet effervesces when placed in an aqueous liquid with an accompanying heat rise which may be as much as 20° C. or more when placed in 200 grams of liquid.

While the present invention has been disclosed with references to certain embodiments, numerous modification, alterations, and changes to the described embodiments are possible without departing from the sphere and scope of the present invention. Accordingly, it is intended that the present invention not be limited to the described embodiments, but that it has the full scope as would be understood by those of skill in the art.

What is claimed is:

1. A composition which, when dissolved in an aqueous liquid, effervesces and raises the temperature of said liquid, comprising an exothermic component selected from the group consisting of magnesium chloride, a zeolite and mixtures thereof, and an effervescent component selected from the group of sodium bicarbonate, potassium bicarbonate, magnesium bicarbonate, calcium bicarbonate and mixtures thereof, said exothermic component and effervescent component being present in amounts sufficient to increase the temperature of 200 ml of water in which said composition is placed by at least 20° C., wherein said composition is free of an organic acid.

2. The composition of claim 1, wherein said composition further comprises at least one of a binder, lubricant, flow aide, surfactant, bleach, enzyme, fragrance, colorant or flavorant.

3. The composition of claim 2, wherein said composition, when dissolved, is effective as a cleaning agent.

4. The composition of claim 2, wherein said composition, when dissolved, is effective as an aroma diffuser.

5. The composition of claim 2, wherein said composition, when dissolved in water, is safe for human topical application.

6. The composition of claim 1, wherein said composition is in the form of a tablet.

7. The composition of claim 1, wherein said composition is in the form of granules.

8. A composition of matter which effervesces in an aqueous solution and raises the temperature of an aqueous solution it is dissolved in, comprising:

Magnesium chloride;

a carbonate salt;

a lubricant; and a bleach;

wherein said composition is free of an organic acid.

9. The composition of claim 8, wherein said composition is in the form of granules.

10. The composition of claim 1, wherein said composition is free of acid.

11. The composition of claim 8, wherein said composition is free of acid.

* * * * *